United States Patent
Overmyer et al.

(10) Patent No.: US 11,471,228 B2
(45) Date of Patent: *Oct. 18, 2022

(54) NEAR FIELD COMMUNICATION BETWEEN A SURGICAL INSTRUMENT AND A ROBOTIC SURGICAL SYSTEM

(71) Applicant: Ethicon LLC, Guaynabo, PR (US)

(72) Inventors: Mark D. Overmyer, Cincinnati, OH (US); Joshua Young, Loveland, OH (US); David C. Yates, West Chester, OH (US); James Hoffmaster, Sharonville, OH (US); Ammon Wright, Portage, MI (US); Vincenzo Barbato, Mason, OH (US)

(73) Assignee: Cilag GmbH International, Zug (CH)

( * ) Notice: Subject to any disclaimer, the term of this patent is extended or adjusted under 35 U.S.C. 154(b) by 220 days.

This patent is subject to a terminal disclaimer.

(21) Appl. No.: 16/890,387

(22) Filed: Jun. 2, 2020

(65) Prior Publication Data

US 2020/0289218 A1 Sep. 17, 2020

Related U.S. Application Data

(63) Continuation of application No. 15/897,877, filed on Feb. 15, 2018, now Pat. No. 10,695,140.

(51) Int. Cl.
*A61B 34/35* (2016.01)
*H04B 5/00* (2006.01)
(Continued)

(52) U.S. Cl.
CPC .......... *A61B 34/35* (2016.02); *A61B 1/00149* (2013.01); *A61B 46/10* (2016.02);
(Continued)

(58) Field of Classification Search
CPC ...... A61B 1/00149; A61B 2017/00221; A61B 2017/00477; A61B 2034/302;
(Continued)

(56) References Cited

U.S. PATENT DOCUMENTS 7,143,925 B2 12/2006 Shelton, IV et al.
8,317,070 B2 11/2012 Hueil et al.
(Continued)

FOREIGN PATENT DOCUMENTS

GB 2552855 A1 2/2018
WO WO-2014151621 A1 9/2014
(Continued)

OTHER PUBLICATIONS

U.S. Appl. No. 15/897,877, filed Feb. 15, 2018, Mark Overmyer et al.

(Continued)

*Primary Examiner* — George Manuel
(74) *Attorney, Agent, or Firm* — Mintz Levin Cohn Ferris Glovsky and Popeo, P.C.

(57) ABSTRACT

Various exemplary methods, systems, and devices for near field communication (NFC) between a surgical instrument and a robotic surgical system are provided. In general, a surgical tool is configured to move between different modes of communication with a robotic surgical system to which the tool is releasably and replaceably coupled. The different modes of communication are detectable by the robotic surgical system by the tool's frequency of NFC with the robotic surgical system. The tool includes a mechanism configured to be manipulated by a user of the tool to move the tool between the different modes of communication. The tool operating in a first mode of communication indicates to the robotic surgical system that the tool is operating in a normal state. The tool operating in each of one or more (Continued)

additional modes of communication indicates that the tool is operating in an error state.

20 Claims, 15 Drawing Sheets

(51) Int. Cl.
| | | |
|---|---|---|
| *A61B 1/00* | (2006.01) | |
| *A61B 90/90* | (2016.01) | |
| *A61B 90/98* | (2016.01) | |
| *A61B 46/10* | (2016.01) | |
| *A61B 17/00* | (2006.01) | |
| *A61B 34/30* | (2016.01) | |

(52) U.S. Cl.
CPC .............. *A61B 90/90* (2016.02); *A61B 90/98* (2016.02); *H04B 5/0031* (2013.01); *A61B 2017/00221* (2013.01); *A61B 2017/00477* (2013.01); *A61B 2034/302* (2016.02)

(58) Field of Classification Search
CPC ......... A61B 34/35; A61B 46/10; A61B 90/90; A61B 90/98; H04B 5/0031
See application file for complete search history.

(56) References Cited

U.S. PATENT DOCUMENTS

| | | |
|---|---|---|
| 8,393,514 B2 | 3/2013 | Shelton, IV et al. |
| 9,943,377 B2 | 4/2018 | Yates et al. |
| 2013/0256377 A1 | 10/2013 | Schmid et al. |
| 2014/0305987 A1* | 10/2014 | Parihar ................ A61B 17/282 227/175.2 |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0142012 A1 | 5/2015 | Lohmeier et al. |
| 2015/0272575 A1 | 10/2015 | Leimbach et al. |
| 2015/0351758 A1 | 12/2015 | Shelton, IV et al. |
| 2016/0354173 A1 | 12/2016 | Dachs, II et al. |
| 2017/0296173 A1 | 10/2017 | Shelton, IV et al. |
| 2018/0000543 A1 | 1/2018 | Hibner |
| 2018/0021098 A1 | 1/2018 | Hemphill |
| 2018/0049813 A1 | 2/2018 | Yates et al. |
| 2018/0049835 A1 | 2/2018 | Shelton, IV et al. |
| 2019/0247133 A1 | 8/2019 | Overmyer et al. |

FOREIGN PATENT DOCUMENTS

| | | |
|---|---|---|
| WO | WO-2014151952 A1 | 9/2014 |
| WO | WO-2019043508 A2 | 3/2019 |

OTHER PUBLICATIONS

International Search Report and Written Opinion for PCT/IS2019/050311 dated May 6, 2019 (19 pages).

U.S. Appl. No. 15/422,740 entitled "Resisting Torque in Articulating Surgical Tools" filed Feb. 2, 2017.

\* cited by examiner

NEAR FIELD COMMUNICATION BETWEEN A SURGICAL INSTRUMENT AND A ROBOTIC SURGICAL SYSTEM

CROSS REFERENCE TO RELATED APPLICATIONS

The present application is a continuation of U.S. patent application Ser. No. 15/897,877, now U.S. Pat. No. 10,695,140, entitled "Near Field Communication Between a Surgical Instrument and a Robotic Surgical System" filed Feb. 15, 2018, which is hereby incorporated by reference in its entirety.

FIELD

The present disclosure relates generally to near field communication between a surgical instrument and a robotic surgical system.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, methods, systems, and devices for near field communication between a surgical instrument and a robotic surgical system are provided.

In one aspect, a surgical system is provided that in one embodiment includes a surgical tool including an elongate shaft having an end effector at a distal end thereof. The end effector is configured to be disposed within a body of a patient. The surgical tool is configured to releasably and replaceably couple to a robotic surgical system configured to provide a control signal to the surgical tool. The surgical tool has a housing at a proximal end of the shaft, and the housing has a door configured to move between an open position and a closed position. The door being in the open position causes the surgical tool to operate in a first mode of communication indicating a first state of operation of the surgical tool, and the door being in the closed position causes the surgical tool to operate in a second mode of communication indicating a second state of operation of the surgical tool that is different from the first state of operation.

The surgical system can vary in any number of ways. For example, the surgical tool can have an antenna disposed in the housing and operatively coupled to a circuit including a switch, and the door in the open position can cause the switch to be open and the door in the closed positon can cause the switch to be closed. In at least some embodiments, the switch being open can short the circuit from the antenna. In at least some embodiments, with the switch being open the antenna can be configured to communicate with the robotic surgical system at a first frequency, and with the switch being closed the antenna can be configured to communicate with the robotic surgical system at a second frequency that is different from the first frequency. In at least some embodiments, with the switch being open the antenna can be disabled from communicating with the robotic surgical system, and with the switch being closed the antenna can be configured to communicate with the robotic surgical system using near field communication (NFC).

For another example, the surgical tool can be configured to communicate with the robotic surgical system using NFC.

For yet another example, the door can be manually movable between the open and closed positions.

In another aspect, a surgical method is provided in that in one embodiment includes positioning a distal end of a surgical tool in a body of a patient. The surgical tool is releasably and replaceably coupled to a robotic surgical system. The method also includes transmitting an NFC signal from the surgical tool to the robotic surgical system in a mode of communication based on a position of a door in a housing of the surgical tool that is positioned outside the body of the patient. The door being open corresponds to a first mode of communication indicative of a first state of operation of the surgical tool, and the door being closed corresponds to a second mode of communication indicative of a second state of operation of the surgical tool.

The method can have any number of variations. For example, in the first mode of communication the surgical tool can communicate with the robotic surgical system at a first frequency, and in the second mode of communication the surgical tool can communicate with the robotic surgical system at a second frequency that is different from the first frequency. For another example, in the first mode of communication the surgical tool can communicate with the robotic surgical system using NFC, and in the second mode of communication the surgical tool can be disabled from communicating with the robotic surgical system. For yet another example, the first state of operation can be indicative of the surgical tool operating normally, and the second state of operation can be indicative of the surgical tool operating in an error state. For still another example, the door can be manually movable between being open and closed.

For another example, an antenna can be disposed in the housing and can be operatively coupled to a circuit including a switch, the door being open can cause the switch to be open, and the door being closed can cause the switch to be closed. In at least some embodiments, the switch being open shorts the circuit from the antenna.

In another embodiment, a surgical method includes transmitting a near field communication (NFC) signal from a robotic surgical system to a surgical tool releasably and replaceably coupled to the robotic surgical system, and, based on a response of the surgical tool to the transmitted signal, determining whether the surgical tool is operating in a first state, in which the surgical tool is operating normally, or a second state, in which the surgical tool is operating in an error state. The method also includes, in response to determining that the surgical tool is operating in the second state, adjusting a parameter of the robotic surgical system that controls future transmission of signals from the robotic surgical system to the surgical tool.

The method can vary in any number of ways. For example, the response of the surgical tool can include a second NFC signal transmitted from the surgical tool to the robotic surgical system, and the determining can include determining whether an amplitude of the second NFC signal is within a first amplitude range corresponding to the first state or if the second NFC signal is within a second, different amplitude range corresponding to the second state. For another example, the response of the surgical tool can be a lack of a response signal transmitted from the surgical tool to the robotic surgical system, and the determining can include determining that the surgical tool is operating in the second state due to the lack of the response signal. For yet another example, adjusting the parameter can disable the future transmission of signals from the robotic surgical system to the surgical tool. For another example, adjusting the parameter can disable the future transmission of signals from the robotic surgical system to the surgical tool related to the error state and can allow the future transmission of signals from the robotic surgical system to the surgical tool that are not related to the error state. For still another example, the signal can be an NFC signal.

BRIEF DESCRIPTION OF DRAWINGS

This invention will be more fully understood from the following detailed description taken in conjunction with the accompanying drawings, in which.

DETAILED DESCRIPTION

Figure 1:
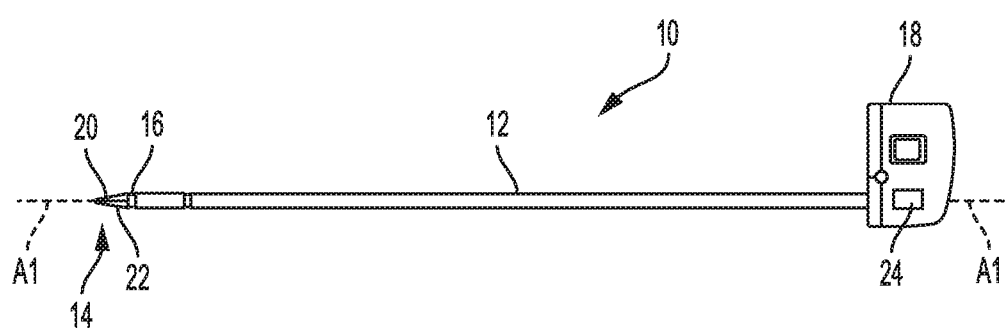
FIG. 1 is a side schematic view of one embodiment of a surgical tool.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "rear" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary methods, systems, and devices for near field communication between a surgical instrument and a robotic surgical system are provided. In general, a surgical tool is configured to move between different modes of communication with a robotic surgical system to which the tool is releasably and replaceably coupled. The different modes of communication are detectable by the robotic surgical system by the tool's frequency of near field communication (NFC) with the robotic surgical system. The tool includes a mechanism, such as a door on a housing of the tool, configured to be manipulated by a user of the tool to move the tool between the different modes of communication. The tool operating in a first mode of communication indicates to the robotic surgical system that the tool is operating in a normal state. The tool operating in each of one or more additional modes of communication indicates that the tool is operating in an error state, with each of the different additional modes of communication indicating a different error state to the robotic surgical system. The robotic surgical system may be able to more safely and/or accurately control the tool by not providing control inputs thereto that would be impossible and/or unsafe for the tool to execute given the tool's error state. The robotic surgical system can be configured to provide a warning indicating the error state, such as by providing a visual alarm on a display of the robotic surgical system, providing an auditory alarm via a speaker of the robotic surgical system, and/or providing another alarm, thereby notifying a user that an error exists to trigger the user to take corrective action to address the error. The tool being configured to move manually between its different modes of communication by the user manipulating the tool's mechanism may allow the user to override the robotic surgical system's control of the tool by moving the tool from a normal state to an error state, thereby providing the user more flexibility in performing a surgical procedure using the tool and/or allowing the user to address any problems with the tool before the robotic surgical system identifies or corrects the problem itself. The user may thereafter return control of the tool to the robotic surgical system by manipulating the mechanism again to move the tool form the error state back to the normal state.

FIG. 1 illustrates one embodiment of a surgical tool 10 that includes an elongate shaft 12, an end effector 14, a wrist 16 that couples the end effector 14 to the shaft 12 at a distal end of the shaft 12, and a tool housing 18 coupled to a proximal end of the shaft 12. The end effector 14 is configured to move relative to the shaft 12 at the wrist 16, e.g., by pivoting at the wrist 16, to position the end effector 14 at a desired location relative to a surgical site during use of the tool 10. In other embodiments, however, the end effector 14 may be in a fixed position relative to the shaft 12. The housing 18 includes various components (e.g., gears and/or actuators) configured to control the operation various features associated with the end effector 14 (e.g., any one or more of clamping, firing, rotation, articulation, energy delivery, etc.). In at least some embodiments, the shaft 12, and hence the end effector 14 coupled thereto, is configured to rotate about a longitudinal axis A1 of the shaft 12. In such embodiments, the various components of the housing 18 are configured to control the rotational movement of the shaft 12. The surgical tool 10 is configured to releasably couple to a robotic surgical system, and the tool housing 18 can include coupling features configured to allow the releasable coupling of the tool 10 to the robotic surgical system. Each of the shaft 12, end effector 14, mist 16, and housing 18 are discussed further below.

The surgical tool 10 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have any of a variety of configurations. In general, the shaft 12 is an elongate member extending distally from the housing 18 and having at least one inner lumen extending therethrough. The shaft 12 is fixed to the housing 18, but in other embodiment the shaft 12 can be releasably coupled to the housing 18 such that the shaft 12 can be interchangeable with other shafts. This may allow a single housing 18 to be adaptable to various shafts having different end effectors.

The end effector 14 can have a variety of sizes, shapes, and configurations. The end effector 14 in this illustrated embodiment includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 in other embodiments can have other configurations, e.g., scissors, a babcock, a retractor, etc.

The wrist 16 of the surgical tool 10 can have any of a variety of configurations. Exemplary embodiments of a wrist of a surgical tool and of effecting articulation at the wrist are described in International Pat. Pub. No. WO 2014/151952 entitled "Compact Robotic Wrist" filed on Mar. 13, 2014, International Pat. Pub. No. WO 2014/151621 entitled "Hyperdexterous Surgical System" filed on Mar. 13, 2014, U.S. Pat. Pub. No. 2018/0000543 entitled "Methods, Systems, And Devices For Initializing A Surgical Tool" filed on Jul. 1, 2016, and U.S. patent application Ser. No. 15/237, 648 entitled "Methods, Systems, And Devices For Causing End Effector Motion With A Robotic Surgical System" filed on Aug. 16, 2016, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., a X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane.

The tool housing 18 can also have a variety of configurations. In general, the tool housing 18 \ includes one or more actuation mechanisms at least partially disposed therein configured to cause movement of the end effector 14 about the wrist 16. The one or more actuation mechanisms can include, for example, one or more movement mechanisms, such as pulley(s), rotors, etc., operably coupled to a plurality of flexible members, e.g., cables, cords, etc., extending along the shaft 12 and configured to be moved to cause translation of the flexible members. The tool housing 18 is configured to be releasably attached to a robotic surgical system (also referred to herein as a "robot" or "surgical robot") so as to releasably attach the tool 10 to the robot. The tool housing 18 can be configured to releasably attach to a robot in any of a variety of ways, as will be appreciated by a person skilled in the art, such as by clamping thereto, clipping thereto, or slidably mating therewith. The one or more movement mechanisms are configured to be controlled by the robot, as will be appreciated by a person skilled in the art, such as by the robot including one or more motors operably coupled to one or more inputs of the tool housing 18 that are operably coupled to the one or more movement mechanisms. The robot includes a computer system that can receive user inputs and can control the motor(s) in response to the user inputs and hence control movement of the flexible members and consequently the end effector 14.

The housing 18 has a door 24 configured to be selectively opened and closed to move the surgical tool 10 between different modes of communication with a robotic surgical system to which the tool 10 is releasably and replaceably coupled. The door 24 is configured to be manually opened and closed by a user of the tool 10, thereby allowing the user to control the state of the tool 10 observed by the robotic surgical system. Communication between a surgical tool, such as the surgical tool 10 of FIG. 1, and a robotic surgical system, is discussed further below. In general, the door 24 being closed corresponds to a first mode of communication in which the surgical tool 10 communicates with the robotic surgical system via NFC at a first frequency. When the door 24 is closed, a switch in a circuit of an antenna of the tool 10 is closed such that the antenna communicates at the first frequency. The first mode of communication corresponds to a normal, default state of the tool 10. The tool 10 communicating with the robotic surgical system at the first frequency can thus indicate to the robotic surgical system that the tool 10 is operating normally. The door 24 is shown closed in FIG. 1. The door 24 being open corresponds to a second mode of communication. The second mode of communication in this illustrated embodiment is the surgical tool 10 being unable to communicate with the robotic surgical system, thereby indicating to the robotic surgical system that the tool 10 is in an error state since the tool 10 cannot respond to any queries from the robotic surgical system by transmit any signals to the robotic surgical system. In other words, opening the door 24 deactivates communication between the robotic surgical system and the tool 10.

In another embodiment, the door 24 being open corresponds to a second mode of communication in which the surgical tool 10 communicates with the robotic surgical system via NFC at a second frequency that is different from the first frequency. Communication between the tool 10 and robotic surgical system is thus not deactivated in this embodiment. When the door 24 is open, the switch in the circuit is open such that the antenna communicates at the second frequency. The tool 10 communicating with the robotic surgical system at the second frequency can thus indicate to the robotic surgical system that the tool 10 is operating abnormally. The robotic surgical system is thus informed of a state of the tool 10 based on whether the tool 10 is communicating with the robotic surgical system over the first frequency or the second frequency. In an exemplary embodiment, the second frequency is higher than the first frequency due to the door 24 being open lowering an amplitude of the communication signal, which corresponds to a higher frequency of the communication signal.

The error state of the tool 10 in the second mode of communication can indicate a variety of errors to the robotic surgical system. For example, the error state can indicate that the tool 10 is unable to receive control signals from the robotic surgical system, e.g., because communication between the tool 10 and robotic surgical system is deactivated. A user may desire to open the door 24 to move the tool 10 from the first mode of communication to the second mode of communication in which communication is deactivated because the user may want to manually bail out the tool 10 due to a malfunction occurring, such as malfunction in the end effector's firing and/or closing. Various embodiments of bailout devices and methods are further described in U.S. patent application Ser. No. 15/237,877 entitled "Robotics Tool Bailouts" filed Aug. 16, 2016, which is hereby incorporated by reference in its entirety. When bailout is complete, the user can close the door 24 to move the tool 10 from the second mode of communication to the first mode of communication. Instead of bail out being desired, a user may desire to prevent, the tool 10 from receiving control signals from the robotic surgical system for another reason, such as if there is an error with another surgical tool that the user believes could be exacerbated or complicated by the tool 10 moving or otherwise responding to a control signal from the robotic surgical system. The user may thus desire to temporarily disable the robotic surgical system's control of the tool 10 until the error with the other surgical tool is addressed.

For another example, the error state can indicate that the end effector 14 does not have a staple cartridge loaded therein, in embodiments in which the tool 10 is a surgical stapler. The robotic surgical system can be configured to prevent staple firing and/or cutting element advancement when the tool 10 is in such an error state. The error state indicating lack of a properly loaded staple cartridge can be communicated at the second frequency, which allows the robotic surgical system to provide certain controls signals to the tool 10 while preventing other control signals that are related to the cartridge, such as staple firing and cutting element advancement. When a staple cartridge is propedy loaded into the end effector 14 the user can close the door 24 to move the tool 10 from the second mode of communication back to the first mode of communication.

For yet another example, the error state can indicate that energy cannot or should not be delivered from the tool 10 to tissue engaged by the end effector 14. A user may desire to prevent energy delivery to tissue for any of a variety for a reasons, such as for safety to prevent energy delivery if an energy activation trigger of the tool 10 is accidentally or prematurely actuated before the desired tissue is engaged or if the user wants the tissue to be cut without any energy applied thereto. The error state indicating an inability to deliver energy can be communicated at the second frequency, which allows the robotic surgical system to provide certain controls signals to the tool 10 while preventing other control signals that cause energy delivery. When energy delivery is desired to be allowed the user can close the door 24 to move the tool 10 from the second mode of communication back to the first mode of communication.

The surgical tool 10 in this illustrated embodiment has a single door 24. Having one door allows the tool 10 to have two modes of communication. In other embodiments, the surgical tool 10, e.g., the housing 18 thereof, can have two or more doors. The number of the tool's modes of communication is defined by $2^{(number\ of\ doors)}$, e.g., one door corresponds to the surgical tool having two modes of communication ($2^1$), two doors corresponds to the surgical tool having four modes of communication ($2^2$), three doors corresponds to the surgical tool having eight modes of communication ($2^3$), four doors corresponds to the surgical tool having sixteen modes of communication ($2^4$), etc. Different combinations of doors being open and closed allows for these various additional modes of communication. Each of a surgical tool's additional modes of communication corresponds to a different state of the surgical tool from each other and from the first and second modes of communication. The robotic surgical system can thus receive more detailed operating state information about the surgical tool when the tool has two or more doors.

When a surgical tool has four or more modes of communication, the surgical tool can include at least one door and at least one other switch control mechanism. For example, the surgical tool can include one door associated with a first switch of the surgical tool and another switch control mechanism associated with a second switch of the surgical tool. In an exemplary embodiment, the surgical tool can include a single door and a different type of switch control mechanism for each additional switch, which may help a user more easily distinguish between the different manually operable mechanisms than if the surgical tool includes doors for each of the switches. Examples of other switch control mechanisms include a rotatable knob, a slidable lever, and a push button.

In at least some embodiments, as mentioned above, the surgical tool 10 can be a stapler. Various embodiments of surgical staplers and uses thereof are further described in U.S. Pat. Pub. No. 2013/0256377 entitled "Layer Comprising Deployable Attachment Members" filed Feb. 8, 2013, U.S. Pat. No. 8,393,514 entitled "Selectively Orientable Implantable Fastener Cartridge" filed Sep. 30, 2010, U.S. Pat. No. 8,317,070 entitled "Surgical Stapling Devices That Produce Formed Staples Having Different Lengths" filed Feb. 28, 2007, U.S. Pat. No. 7,143,925 entitled "Surgical Instrument Incorporating EAP Blocking Lockout Mechanism" filed Jun. 21, 2005, U.S. Pat. Pub. No. 2015/0134077 entitled "Sealing Materials For Use In Surgical Stapling" filed Nov. 8, 2013, U.S. Pat. Pub. No. 2015/0134076, entitled "Hybrid Adjunct Materials for Use in Surgical Stapling" filed Nov. 8, 2013, U.S. Pat. Pub. No. 2015/0133996 entitled "Positively Charged Implantable Materials and Method of Forming the Same" filed Nov. 8, 2013, U.S. Pat. Pub. No. 2015/0129634 entitled "Tissue Ingrowth Materials and Method of Using the Same" filed Nov. 8, 2013, U.S. Pat. Pub. No. 2015/0133995 entitled "Hybrid Adjunct Materials for Use in Surgical Stapling" filed Nov. 8, 2013, U.S. Pat. Pub. No. 2015/0272575 entitled "Surgical Instrument Comprising a Sensor System" filed Mar. 26, 2014, U.S. Pat. Pub. No. 2015/0351758 entitled "Adjunct Materials and Methods of Using Same in Surgical Methods for Tissue Sealing" filed Jun. 10, 2014, and U.S. patent application Ser. No. 15/422,740 entitled "Resisting Torque In Articulating Surgical Tools" filed Feb. 2, 2017, which are hereby incorporated by reference in their entireties.

As will be appreciated by a person skilled in the art, electronic communication between various integral components of and components removably connected to a robotic surgical system can be wired or wireless. A person skilled in the art will also appreciate that all electronic communication in the robotic surgical system can be wired, all electronic communication in the robotic surgical system can be wireless, or some portions of the robotic surgical system can be in wired communication and other portions of the system can be in wireless communication.

Figure 2:
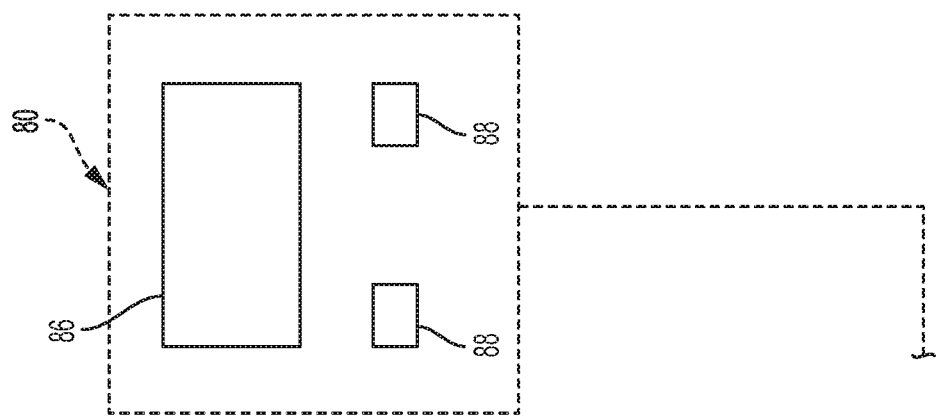
FIG. 2 is a perspective view of one embodiment of a robotic surgical system that includes a patient-side portion and a user-side portion.
Figure 2:
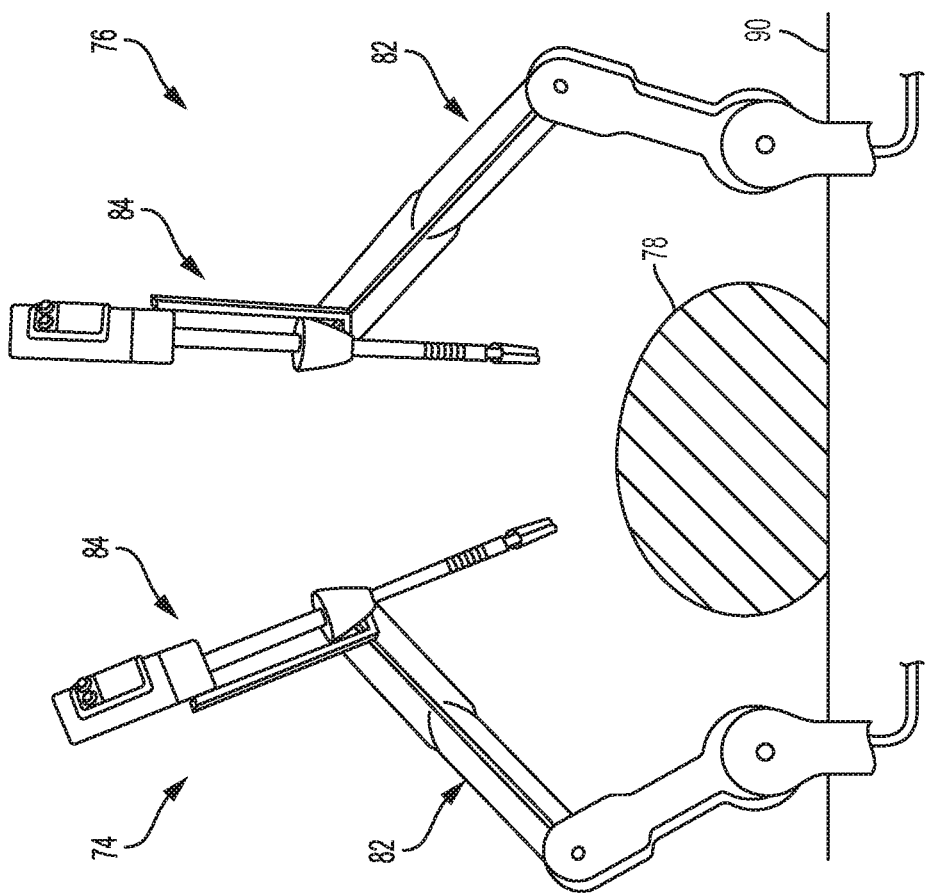

FIG. 2 is a perspective view of one embodiment of a robotic surgical system 74 that includes a patient-side portion 76 that is positioned adjacent to a patient 78, and a user-side portion 80 that is located a distance from the patient, either in the same room and/or in a remote location. The patient-side portion 76 generally includes one or more robotic arms 82 and one or more tool assemblies 84 that are configured to releasably couple to a robotic arm 82. The user-side portion 76 generally includes a vision system 86 for viewing the patient 78 and/or surgical site, and a control system 88 for controlling the movement of the robotic arms 108 and each tool assembly 84 during a surgical procedure.

The control system 88 can have a variety of configurations and can be located adjacent to the patient (e.g., in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 88 can include components that enable a user to view a surgical site of the patient 78 being operated on by the patient-side portion 76 and/or to control one or more parts of the patient-side portion 76 (e.g., to perform a surgical procedure at the surgical site), In some embodiments, the control system 88 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 82 and tool assemblies 84.

The patient-side portion 76 can have a variety of configurations. As illustrated in FIG. 2, the patient-side portion 76 can couple to an operating table 90. However, in other embodiments, the patient-side portion 76 can be mounted to a wall, to the ceiling, to the floor, or to other operating room equipment. Further, while the patient-side portion 76 is shown as including two robotic arms 82, more or fewer robotic arms 82 may be included. Furthermore, the patient-side portion 76 can include separate robotic arms 82 mounted in various positions, such as relative to the surgical table 90 (as shown in FIG. 2). Alternatively, the patient-side portion 76 can include a single assembly that includes one or more robotic arms 82 extending therefrom.

Figure 3:
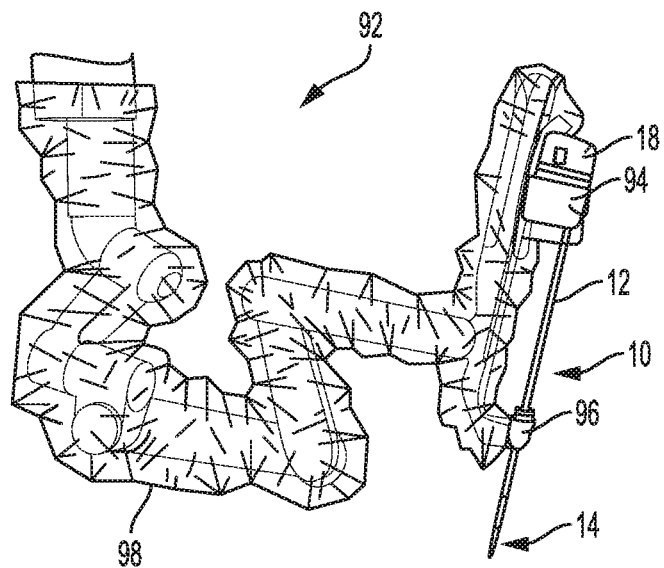
FIG. 3 is a perspective view of one embodiment of a robotic arm of a robotic surgical system with the surgical tool of FIG. 1 releasably and replaceably coupled to the robotic arm.

FIG. 3 illustrates another embodiment of a robotic arm 92 and the surgical tool 10 of FIG. 1 releasably and replaceably coupled to the robotic arm 92, although other surgical tools can be similarly releasably and replaceably coupled thereto. The robotic arm 92 is configured to support and move the associated tool 10 along one or more degrees of freedom (e.g., all six Cartesian degrees of freedom, five or fewer Cartesian degrees of freedom, etc.).

The robotic arm 92 includes a tool driver 94 at a distal end of the robotic arm 92, which can assist with controlling features associated with the tool 10. The robotic arm 92 also includes an entry guide 96 (e.g., a cannula mount, cannula, etc) that can be a part of or releasably and replaceably coupled to the robotic arm 92, as shown in FIG. 3. A shaft of a tool assembly can be inserted through the entry guide 96 for insertion into a patient, as shown in FIG. 3 in which the shaft 12 of the tool 10 of FIG. 1 is shown inserted through the entry guide 96.

In order to provide a sterile operation area while using the surgical system, a barrier 98 can be placed between the actuating portion of the surgical system (e.g., the robotic arm 92) and the surgical instruments coupled thereto (e.g., the tool 10, etc.). A sterile component, such as an instrument sterile adapter (ISA), can also be placed at the connecting interface between the tool 10 and the robotic arm 92. The placement of an ISA between the tool 10 and the robotic arm 92 can ensure a sterile coupling point for the tool 10 and the robotic arm 92. This permits removal of surgical instruments from the robotic arm 92 to exchange with other surgical instruments during the course of a surgery without compromising the sterile surgical field.

Figure 4:
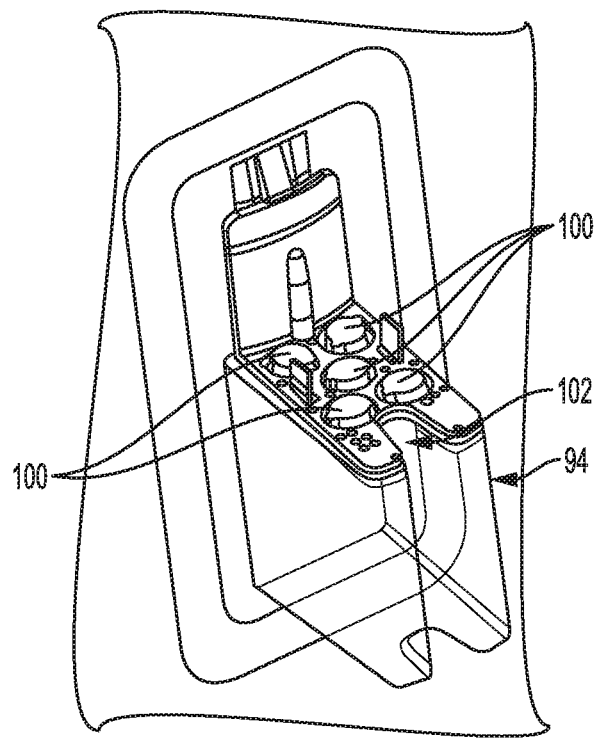
FIG. 4 is a perspective view of a tool driver of the robotic arm of FIG. 3.

FIG. 4 illustrates the tool driver 94 in more detail. As shown, the tool driver 94 includes one or more motors, e.g., five motors 100 are shown, that control a variety of movements and actions associated with the tool 10 coupled to the arm 92. For example, each motor 100 can couple to and/or interact with an activation feature (e.g., gear) associated with the tool 10 for controlling one or more actions and movements that can be performed by the tool 10, such as for assisting with performing a surgical operation. The motors 100 are accessible on the upper surface of the tool driver 94, and thus the tool 10 (e.g., the housing 18 thereof) is configured to mount on top of the tool driver 94 to couple thereto. Exemplary embodiments of motor operation and components of a tool housing (also referred to as a "puck") configured to controlled by tool driver motors are further described in previously mentioned International Pat. Pub. No. WO 2014/151952 entitled "Compact Robotic Wrist" filed Mar. 13, 2014 and International Pat. Pub. No. WO 2014/151621 entitled "Hyperdexterous Surgical System" filed Mar. 13, 2014, U.S. Pat. Pub. No. 2018/0000543 entitled "Methods, Systems, And Devices For Initializing A Surgical Tool" filed Jul. 1, 2016, and in U.S. patent application Ser. No. 15/237,653 entitled "Methods, Systems, And Devices For Controlling A Motor Of A Robotic Surgical Systems" filed Aug. 16, 2016, which is hereby incorporated by reference in its entirety.

The tool driver 94 also includes a shaft-receiving channel 102 formed in a sidewall thereof for receiving a tool shaft, e.g., the shaft 12 of the tool 10. In other embodiments, the shaft can extend through an opening in the tool driver 122, or the two components can mate in various other configurations.

Figure 5:
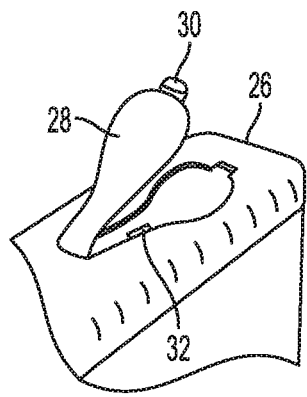
FIG. 5 is a perspective view of a portion of a tool housing of another embodiment of a surgical tool.

FIG. 5 illustrates another embodiment of a tool housing 26 of a surgical tool that includes a door 28. The surgical tool of FIG. 5 is generally configured and used similar to the tool 10 of FIG. 1, e.g., includes an elongate shaft, an end effector, a wrist, etc. The door 28 in this illustrated embodiment includes a tab 30 to facilitate user handling and opening of the door 28. The door 28 is configured to selectively engage a switch 32 in a circuit of an antenna of the tool. The door 28 has an inner surface (obscured in FIG. 5) configured to press on the switch 32 when the door 28 is closed, thereby holding the switch 32 in a closed position. When the door 28 is open, the door's inner surface is not pressing on the switch 32 such that the switch is open. The door 28 is shown open in FIG. 5.

Figure 6:
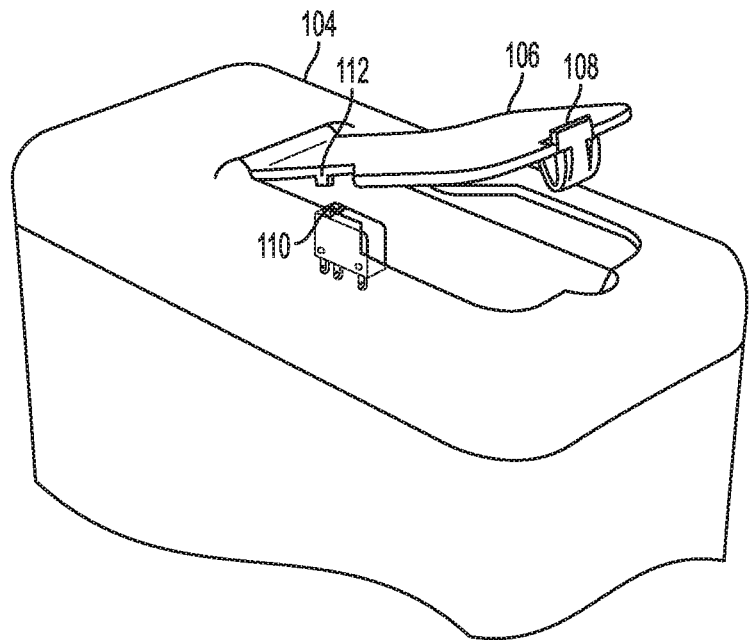
FIG. 6 is a perspective view of one embodiment of a switch and a portion of a tool housing of yet another embodiment of a surgical tool.

FIG. 6 illustrates another embodiment of a tool housing 104 of a surgical tool that includes a door 106. The surgical tool of FIG. 6 is generally configured and used similar to the tool 10 of FIG. 1, e.g., includes an elongate shaft, an end effector, a wrist, etc. The door 106 in this illustrated embodiment includes a tab 108 to facilitate user opening of the door 106. The door 106 is configured to selectively engage a switch 110 in a circuit of an antenna of the tool. The door 106 has a projection 112 extending in a direction toward the switch 110 that is configured to selectively press on the switch 110 based on whether the door 106 is open or closed. An inner surface of the door 106 configured to selectively press the switch 110 in this illustrated embodiment is thus a surface of the protrusion 112. The protrusion 112 presses on the switch 110 when the door 106 is closed such that the switch 110 is closed. The protrusion 112 does not press on the switch 110 when the door 106 is open such that the switch 110 is open. The door 106 is shown open in FIG. 6.

Figure 7:
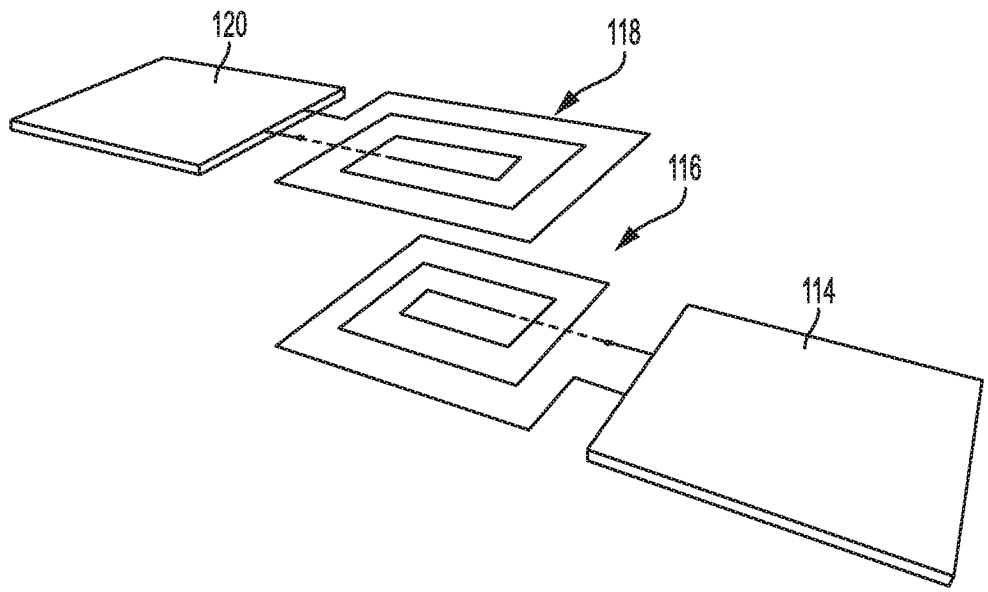
FIG. 7 is a schematic view of a circuit and antenna of a robotic surgical system and a circuit and antenna of a surgical tool.

FIG. 7 illustrates an embodiment of a surgical tool circuit 114 including a switch, such as the switch 110 of FIG. 6, operatively connected to an antenna 116 of the surgical tool.

The tool's antenna 116 is configured to communicate via NFC with an antenna 118 of the robotic surgical system that is operatively connected to a drive circuit 120 of the robotic surgical tool.

Figure 8:
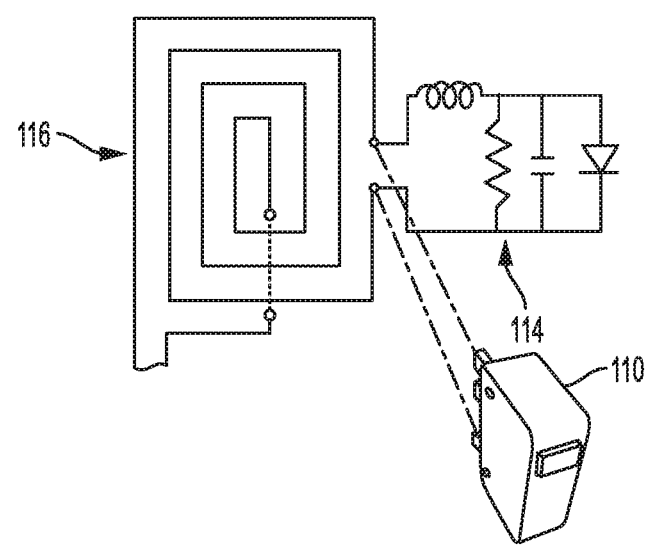
FIG. 8 is a partially schematic view of one embodiment of a circuit and antenna of a surgical tool, the circuit including the switch of FIG. 6.
Figure 9:
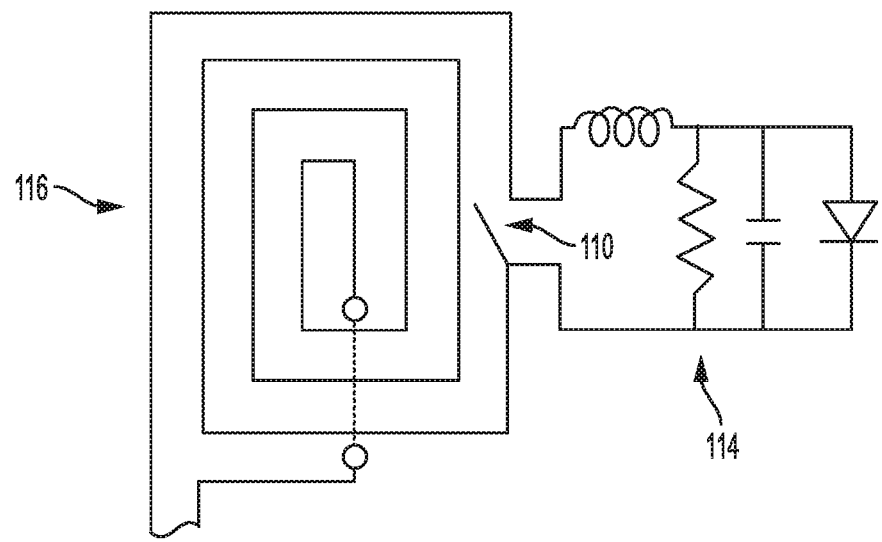
FIG. 9 is a schematic view of the circuit and antenna of FIG. 8.

FIGS. 8 and 9 illustrate an embodiment of the tool circuit 114. The switch of the circuit 114 in FIG. 8 is shown as the switch 110 of FIG. 6, although other switches and other surgical tools can be similarly used. FIG. 9 illustrates the switch 110 schematically and in the open position. The circuit 114 in this illustrated embodiment is a passive oscillator. The switch 110 is configured to selectively include with or short the passive oscillator from the antenna 116. When the switch 110 is in the closed position, the passive oscillator is not shorted and the antenna 116 can communicate via NFC at a first frequency. When the switch 110 is in the open position, the passive oscillator is shorted and the antenna 116 can communicate via NFC at a second frequency that is different from the first frequency.

Figure 10:
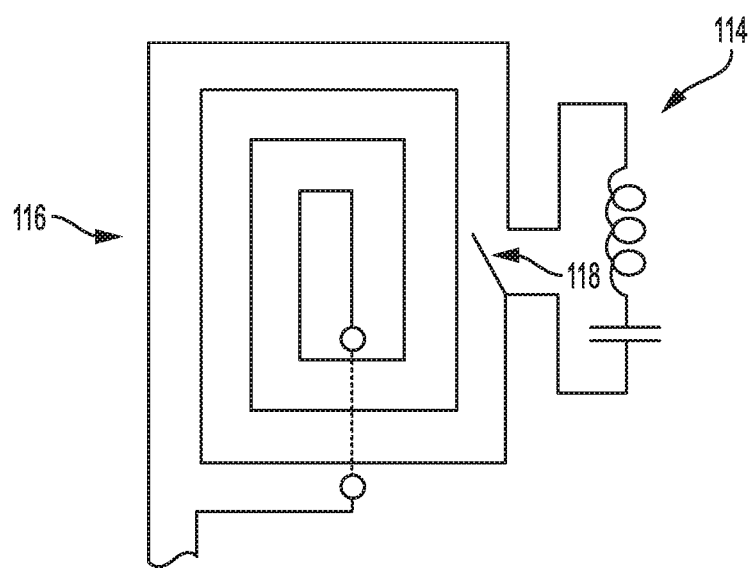
FIG. 10 is a schematic view of another embodiment of a circuit and antenna of a surgical tool.

FIG. 10 illustrates another embodiment of the tool circuit 114 that includes a switch 118, such as the switch 110 of FIG. 6. FIG. 10 illustrates the switch 118 in the open position. The circuit 114 in this illustrated embodiment is a series LC filter. The switch 118 is configured to selectively include or short the series LC filter. When the switch 118 is in the closed position, the series LC filter is not shorted and the antenna 116 can communicate via NFC at a first frequency. When the switch 118 is in the open position, the series LC filter is shorted and the antenna 116 can communicate via NFC at a second frequency that is different from the first frequency.

Figure 11:
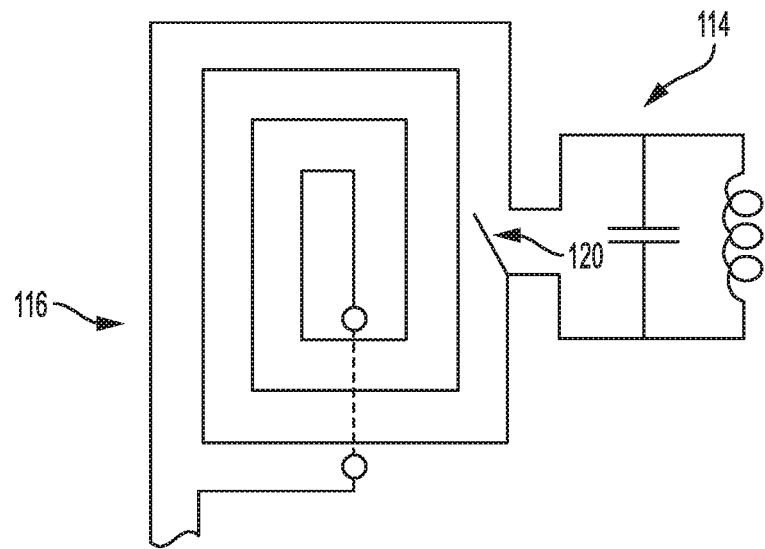
FIG. 11 is a schematic view of yet another embodiment of a circuit and antenna of a surgical tool.

FIG. 11 illustrates another embodiment of the tool circuit 114 that includes a switch 120, such as the switch 110 of FIG. 6. FIG. 11 illustrates the switch 120 in the open position. The circuit 114 in this illustrated embodiment is a parallel LC filter. The switch 120 is configured to selectively include or short the parallel LC filter. When the switch 120 is in the closed position, the parallel LC filter is not shorted and the antenna 116 can communicate via NFC at a first frequency. When the switch 120 is in the open position, the parallel LC filter is shorted and the antenna 116 can communicate via NFC at a second frequency that is different from the first frequency.

Figure 12:
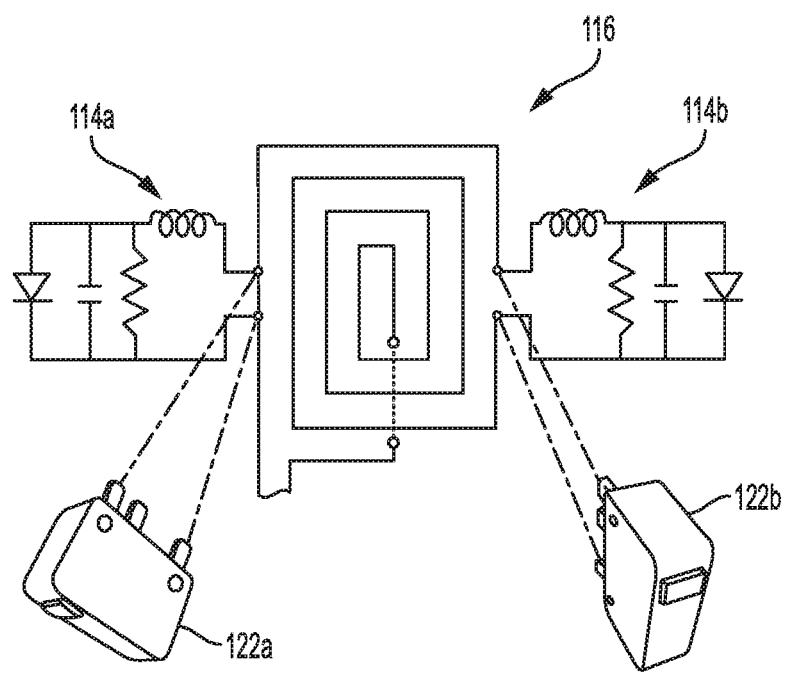
FIG. 12 is a partially schematic view of another embodiment of a circuit and antenna of a surgical tool, the circuit including two switches of FIG. 6.

FIG. 12 illustrates an embodiment of the tool circuit 114 that includes a first circuit 114a including a first switch 122a and a second circuit 114b including a second switch 112b. Each of the switches 112a, 112b are shown as being the same type as the switch 110 of FIG. 6, but other switches can be similarly used. Each of the circuits 114a, 114b in this illustrated embodiment includes a passive oscillator. As discussed above, a first door (or other switch control mechanism) of a tool housing can be configured to selectively open and close the first switch 122a, and a second door (or other switch control mechanism) of the tool housing can be configured to selectively open and close the second switch 122b. As also discussed above, the first and second circuits 114a, 114b allow the surgical tool to have four modes of communication including a first mode in which both switches 122a, 122b are closed, a second mode in which both switches 122a, 122b are open, a third mode in which the first switch 122a is closed and the second switch 122b is open, and a fourth mode in which the first switch 122a is open and the second switch 122b is closed. In each of the four modes of communication, the tool's antenna 116 communicates with the robotic surgical system to which the tool is releasably and replaceably coupled at a different frequency, thereby allowing the robotic surgical system to identify a state of the tool based on the frequency of communication.

Figure 13:
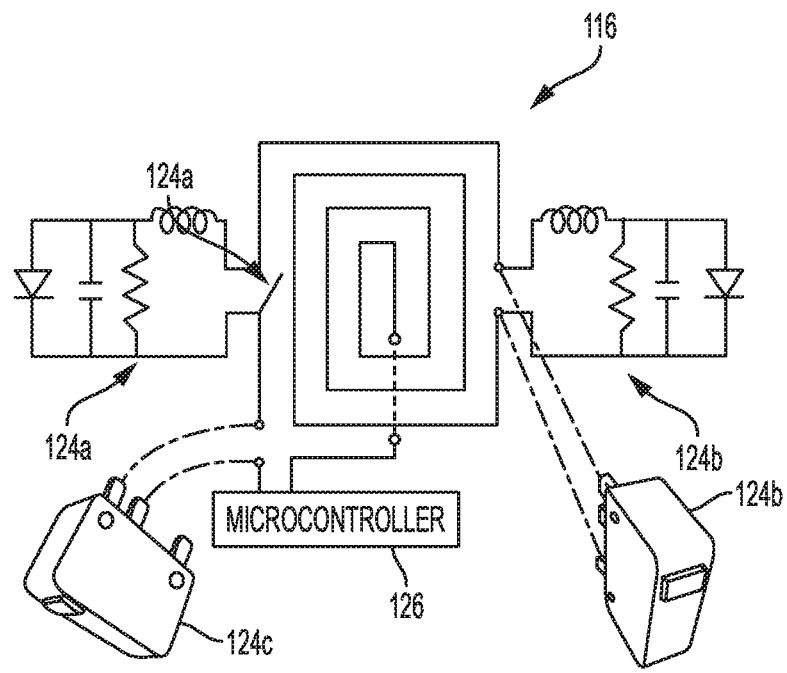
FIG. 13 is a partially schematic view of yet another embodiment of a circuit and antenna of a surgical tool, the circuit including two switches of FIG. 6 and including a microcontroller.

FIG. 13 illustrates another embodiment of the tool circuit 114 that includes a first circuit 114a including a first switch 124a and a second circuit 114b including a second switch 124b. Each of the circuits 124a, 124b in this illustrated embodiment includes a passive oscillator. As discussed above, a first door (or other switch control mechanism) of a tool housing can be configured to selectively open and close the first switch 124a, and a second door (or other switch control mechanism) of the tool housing can be configured to selectively open and close the second switch 124b. In this illustrated embodiment, a third switch 124c is configured to selectively open and close to selectively attach a microcontroller 126 (e.g., a processor, etc.) to the antenna 116 for NFC and power. Each of the antennas illustrated in various figures herein are operatively connected to a microcontroller for NFC and power even when the microcontroller is not specifically illustrated. When the third switch 124c is closed, the microcontroller 126 provides NFC and power to the antenna 116 to allow the surgical tool to communicate with the robotic surgical system to which the tool is releasably and replaceably coupled. When the third switch 124c is open, the microcontroller 126 does not provide NFC or power to the antenna 116 so as to prevent the surgical tool from communicating with the robotic surgical system. As discussed above, the first and second circuits 124a, 124b allow the surgical tool to have four modes of communication each at a different frequency, with the third switch 124c providing a fifth mode of communication in which communication with the robotic surgical system is deactivated. As also discussed above, in some embodiments, the only switch of a surgical tool can be a switch for selectively deactivating communication, e.g., a switch for deactivating a microcontroller similar to the switch 124c for deactivating the microcontroller 126 of FIG. 13. The first and third switches 124a, 124c are shown as each being the same type as the switch 110 of FIG. 6, but other switches can be similarly used. The second switch 124b is shown schematically and can be the same type as the switch 110 of FIG. 6 or be another type of switch.

Figure 14:
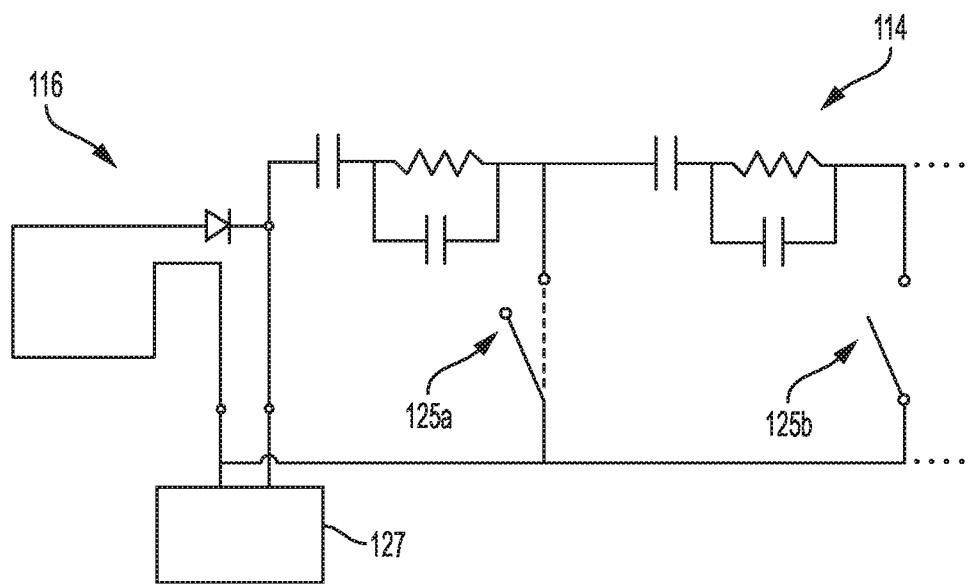
FIG. 14 is a schematic view of another embodiment of a circuit and antenna of a surgical tool.

FIG. 14 illustrates another embodiment of the tool circuit 114 that includes a first circuit 114a including a first switch 125a and a second circuit 114b including a second switch 125b. One or more additional switches are possible in the circuit 114, as indicated by the dotted lines trailing from the right of FIG. 14. As discussed above, a first door (or other switch control mechanism) of a tool housing can be configured to selectively open and close the first switch 125a, and a second door (or other switch control mechanism) of the tool housing can be configured to selectively open and close the second switch 125b. As discussed above, the first and second circuits 125a, 125b allow the surgical tool to have four modes of communication each at a different frequency. Similar to the embodiment of FIG. 13, a microcontroller 127 is attached to the antenna 116 for NFC and power. However, unlike the embodiment of FIG. 13, the microcontroller 127 does not have a switch associated therewith such that the microcontroller 127 is continuously available for NFC and power.

Figure 15:
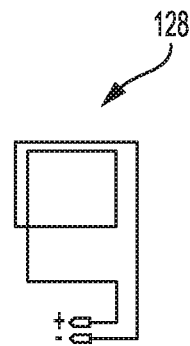
FIG. 15 is a schematic view of a traditional NFC antenna.
Figure 16:
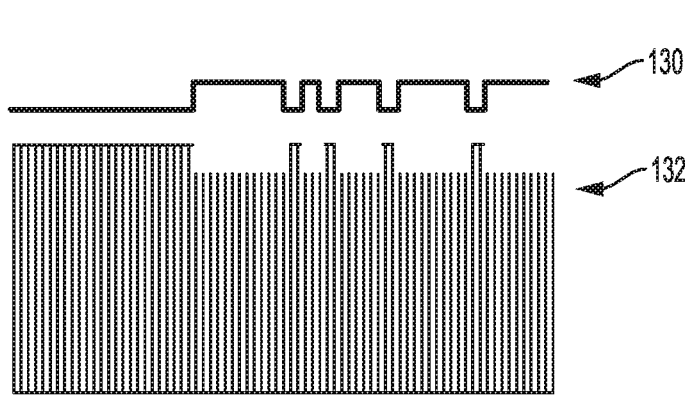
FIG. 16 is a representation of a data signal and a carrier wave carrying the data signal using the antenna of FIG. 15.

FIG. 15 illustrates a traditional NFC antenna 128 for a device, and FIG. 16 illustrates a corresponding data waveform 130 for communication from the device and a carrier wave 132 from the antenna 128 that carries the data 130. The carrier wave 132 in this illustrated embodiment has a frequency of 13.56 MHz and has 10% modulation. For comparison purposes, FIGS. 17-28 are discussed below with respect to the data waveform 130. In other words, the various antennas of FIGS. 17, 19, 21, 23, 25, and 27 are discussed below as communicating the data waveform 130 to facilitate comparison of the various carrier waves of FIGS. 18, 20, 22, 24, 26, and 28 with respect to the carrier wave 132 of FIG. 16 and various ones of each other.

Figure 17:
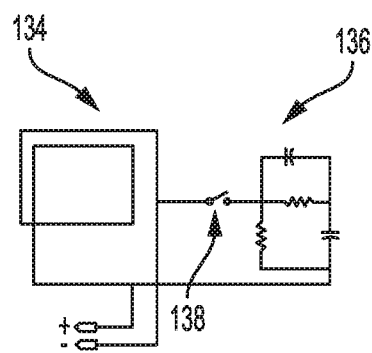
FIG. 17 is a schematic view of one embodiment of a circuit and antenna with a switch of the circuit in an open position.
Figure 18:
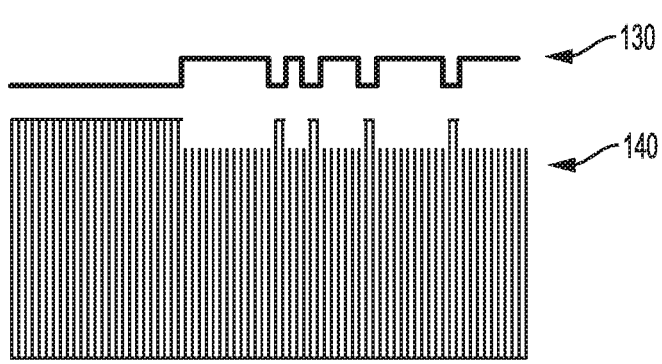
FIG. 18 is a representation of the data signal of FIG. 16 and a carrier wave carrying the data signal using the antenna of FIG. 17.
Figure 19:
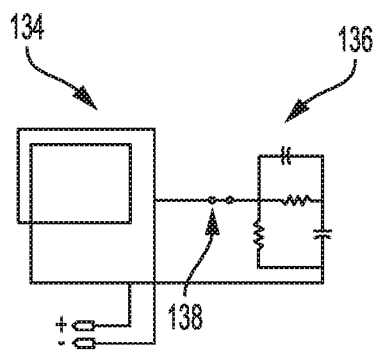
FIG. 19 is a schematic view of the circuit and antenna of FIG. 17 with the switch in a closed position.
Figure 20:
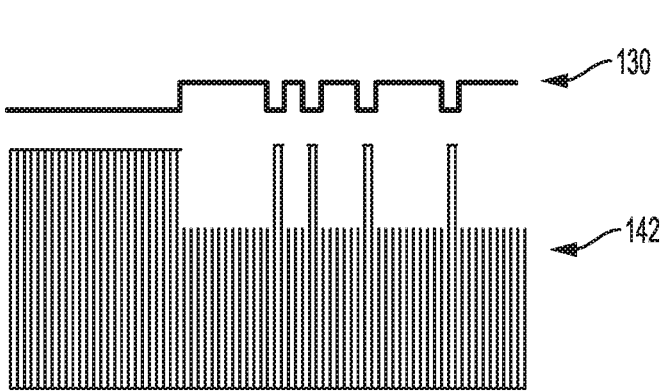
FIG. 20 is a representation of the data signal of FIG. 16 and a carrier wave carrying the data signal using the antenna of FIG. 19.

FIG. 17 illustrates an antenna 134 of a surgical tool as described herein that includes a circuit 136 and a switch 138 that selectively includes and shorts the circuit 136 with the antenna 134. The circuit 136 in this illustrated embodiment includes two resistors and two capacitors, although another combination of resistors alone, capacitors alone, or another combination of resistors and capacitors can be used. The switch 138 is open in FIG. 17, so, as shown in FIG. 18, a carrier wave 140 carrying the data 130 is the same as the carrier wave 132 of FIG. 16 since the antenna 134 is operating as if the circuit 136 is not present. In other words, the circuit 136 is shorted. FIG. 19 illustrates the circuit 136 with the switch 138 closed, so the modulation of a carrier wave 142 carrying the data 130 is increased in FIG. 20 from the carrier wave 140 of FIG. 18 with the amplitude of the carrier wave 142 being reduced. The transmission of the data 130 thus indicates to a robotic surgical system releasably and replaceably coupled to the surgical tool of a state of the surgical tool based on whether the data is received by the robotic surgical system at the first frequency (switch 138 closed, FIG. 20) or the second frequency (switch 138 open, FIG. 18). The modulation of the carrier wave 142 of FIG. 20 is increased to 20% from the 10% modulation of the carrier wave 140 of FIG. 18, but other amounts of increase are possible. In an exemplary embodiment, the amount of increase is at least 5%, which may help the robotic surgical system accurately differentiate between different frequencies.

Figure 21:
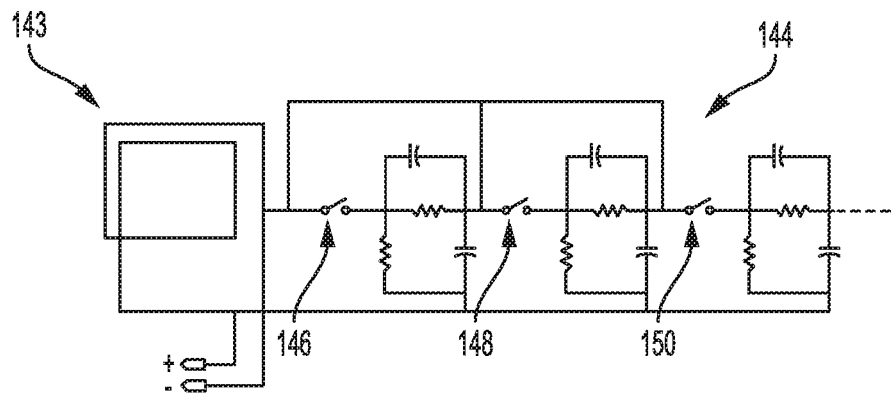
FIG. 21 is a schematic view of one embodiment of a circuit and antenna with each switch of the circuit in an open position.
Figure 22:
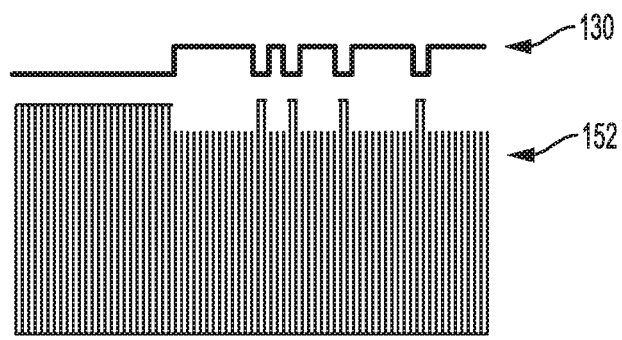
FIG. 22 is a representation of the data signal of FIG. 16 and a carrier wave carrying the data signal using the antenna of FIG. 21.
Figure 23:
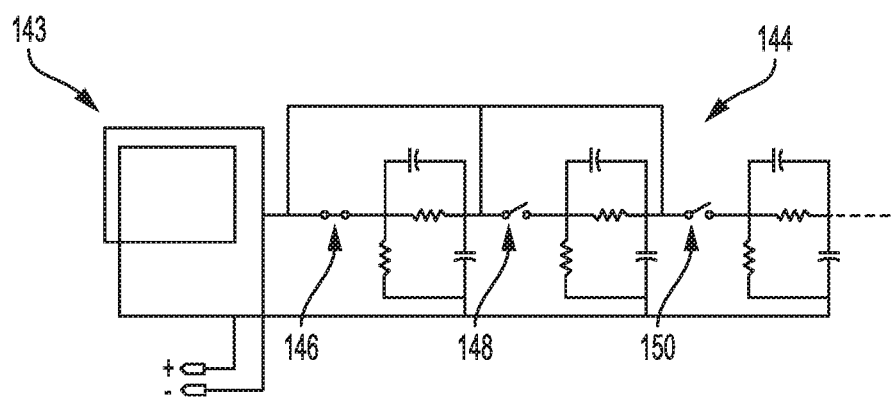
FIG. 23 is a schematic view of the circuit and antenna of FIG. 21 with two of the switches in an open position and one of the switches in a closed position.
Figure 24:
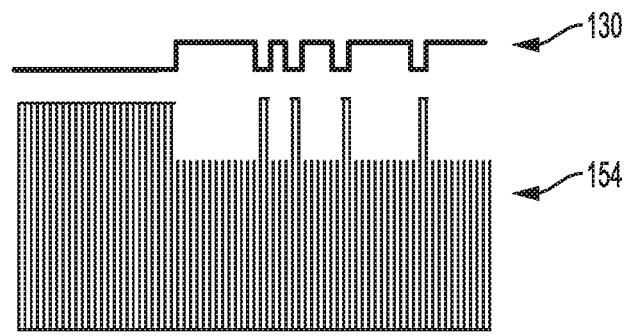
FIG. 24 is a representation of the data signal of FIG. 16 and a carrier wave carrying the data signal using the antenna of FIG. 23.
Figure 25:
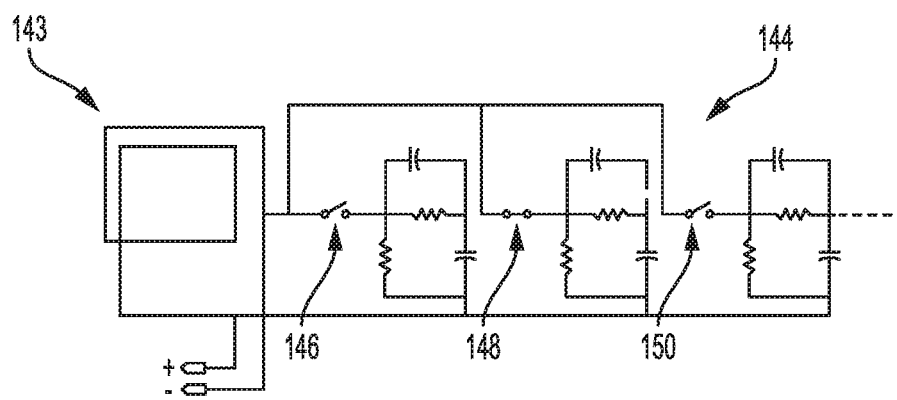
FIG. 25 is a schematic view of the circuit and antenna of FIG. 21 with another two of the switches in an open position and another one of the switches in a closed position.
Figure 26:
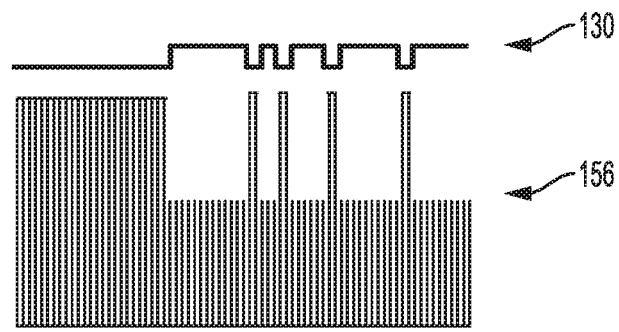
FIG. 26 is a representation of the data signal of FIG. 16 and a carrier wave carrying the data signal using the antenna of FIG. 25.
Figure 27:
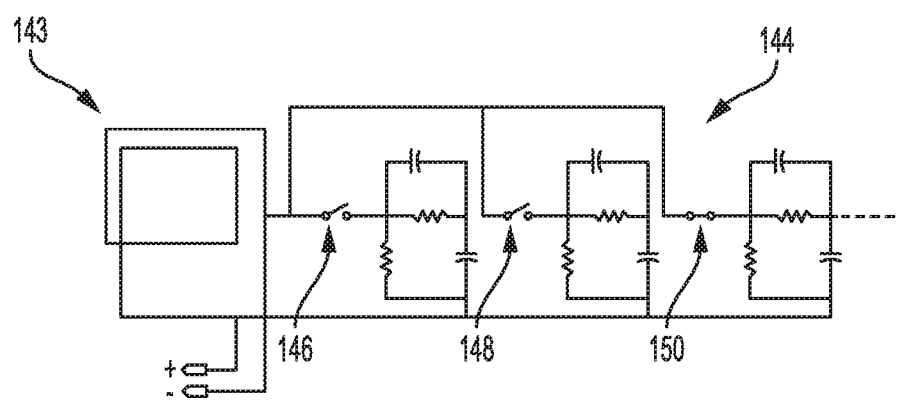
FIG. 27 is a schematic view of the circuit and antenna of FIG. 21 with yet another two of the switches in an open position and yet another one of the switches in a closed position.
Figure 28:
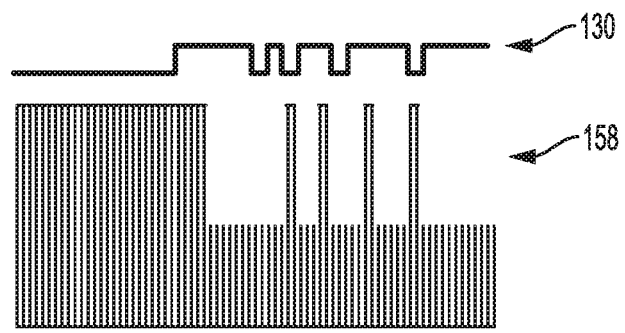
FIG. 28 is a representation of the data signal of FIG. 16 and a carrier wave carrying the data signal using the antenna of FIG. 27.

FIG. 21 illustrates an antenna 143 of a surgical tool as described herein that includes a circuit 144 including first, second, and third switches 146, 148, 150. One or more additional switches are possible for the circuit 144, as indicated by the dotted lines trailing from the right of FIG. 21. The switches 146, 148, 150 are all open in FIG. 21, so, as shown in FIG. 22, a carrier wave 152 carrying the data 130 is the same as the carrier wave 132 of FIG. 16 since the antenna 143 is operating if the circuit 144 is not present. FIG. 23 illustrates the first switch 146 closed and the second and third switches 148, 150 open, so the modulation of a carrier wave 154 carrying the data 130 is increased in FIG. 24 from FIG. 22, e.g., increased from 10% to 20%, with the amplitude of the carrier wave 154 being reduced. FIG. 25 illustrates the second switch 148 closed and the first and third switches 146, 150 open, so the modulation of a carrier wave 156 carrying the data 130 is increased in FIG. 26 from FIG. 24, e.g., increased from 20% to 40%, with the amplitude of the carrier wave 156 being reduced. FIG. 27 illustrates the third switch 150 closed and the first and second switches 146, 148 open, so the modulation of a carrier wave 158 carrying the data 130 is increased in FIG. 28 from FIG. 26, e.g., increased from 40% to 60%, with the amplitude of the carrier wave 158 being reduced. FIGS. 21-28 thus illustrate four modes of communication of the surgical tool. Because there are three switches, four additional modes of communication are possible, for a total of eight modes, based on various combinations of the switches 146, 148, 150 being open and closed: the first and second switches 146, 148 closed and the third switch 150 open, the first and third switches 146, 150 closed and the second switch 148 open, the second and third switches 148, 150 closed and the first switch 146 open, and all three switches 146, 148, 150 closed. When all three switches 146, 148, 150 are closed, the amplitude of the resulting carrier wave may be too small for successful transmission of the data 130. The values of the various resistors and capacitors in the circuit 144 can be adjusted so that the carrier wave can be large enough for transmission of the data 130 when all three switches 146, 148, 150 are closed. As discussed above, each of the modes of communication can be associated with a different frequency to facilitate the robotic surgical system's identification of the surgical tool's state.

Figure 29:
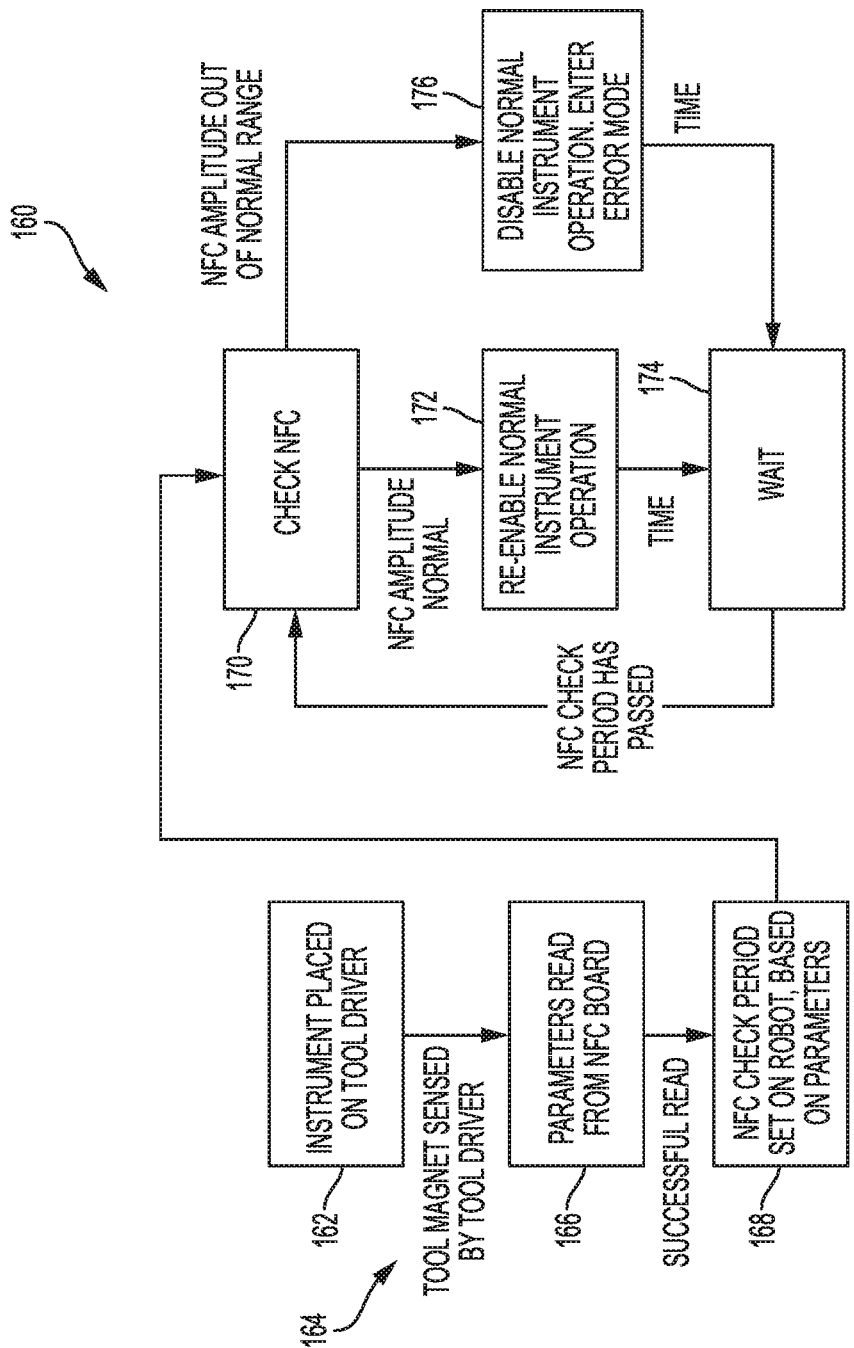
FIG. 29 is a flowchart of one embodiment of a method including communication from a surgical tool to a robotic surgical system.

FIG. 29 illustrates one embodiment of a method 160 of using a surgical tool that includes at least one door (or other switch control mechanism) configured to be selectively opened and closed to move the surgical tool 10 between different modes of communication with a robotic surgical system to which the tool 10 is releasably and replaceably coupled. Although the method 160 of FIG. 29 is discussed with respect to the surgical tool 10 of FIG. 1 and the robotic surgical system 74 of FIG. 4, any of the surgical tools and robotic surgical systems described herein can be similarly used.

In general, in the method 160 of FIG. 29, once the tool 10 is removably coupled to the robotic surgical system 74, the robotic surgical system 74 reads parameters of the tool 10 and then the tool 10 is operated normally until the robotic surgical system 74 detects a change in the tool's NFC signal to the robotic surgical system 74, e.g., a change in the signals amplitude or power. The change in the tool's NFC signal is due to the tool's door 24 being opened by a user which electrically altered the tool's antenna.

More particularly, in the method 160 the tool 10 is removably coupled 162 to the robotic surgical system 74 by coupling the tool's housing 18 to one of the robotic surgical system's arms 82. The tool's coupling 162 to the arm 82 is sensed 164 by the robotic surgical system 74 by, e.g., sensing a magnet on the housing 18. The robotic surgical system 74 reads 166 parameters of the tool 10, e.g., type of tool, size of tool, etc., via NFC communication with the tool 10, as will be appreciated by a person skilled in the art. After the parameters are read 166 successfully, the robotic surgical system 74 sets 168 a schedule for NFC communication checks with the tool 10 based on the parameters of the tool 10, as will also be appreciated by a person skilled in the art.

When the robotic surgical system 74 communicates via NFC with the tool 10, the robotic surgical system 74 checks 170 the NFC communication from the tool 10 to determine whether or not the communication is normal or abnormal. In other words, the robotic surgical system 74 determines the tool's mode of communication. If the communication is determined to be normal, e.g., if the tool 10 is operating in a first mode of communication as indicated by an amplitude of the NFC signal from the tool 10, then the robotic surgical system 74 enables (or re-enables) 172 normal operation of the tool 10 in which the robotic surgical system 74 transmits control signals to the tool 10 under normal operating procedures. Time then passes and the robotic surgical system 74 waits 174 for the set 168 time period between NFC communication checks to pass before again checking 170 the NFC communication from the tool 10. If, instead, the communication is determined to be abnormal, e.g., if the tool 10 is operating in a second mode of communication as indicated by an amplitude of the NFC signal from the tool 10, the robotic surgical system 74 disables 176 normal operation of the tool and enters an error mode in which the robotic surgical system 74 cannot normally operate the tool 10, e.g., because operating the tool 10 normally could endanger the patient or otherwise cause problem(s) given the tool's current condition. Time then passes and the robotic surgical system 74 waits 174 for the set 168 time period between NFC communication checks to pass before again checking 170 the NFC communication from the tool 10. The robotic surgical system 74 may thus regularly monitor the status of the tool 10 regardless of whether the tool 10 is operating normally or abnormally so the robotic surgical system 74 can adjust its control of the tool 10 as needed based on the tool's current status.

Figure 30:
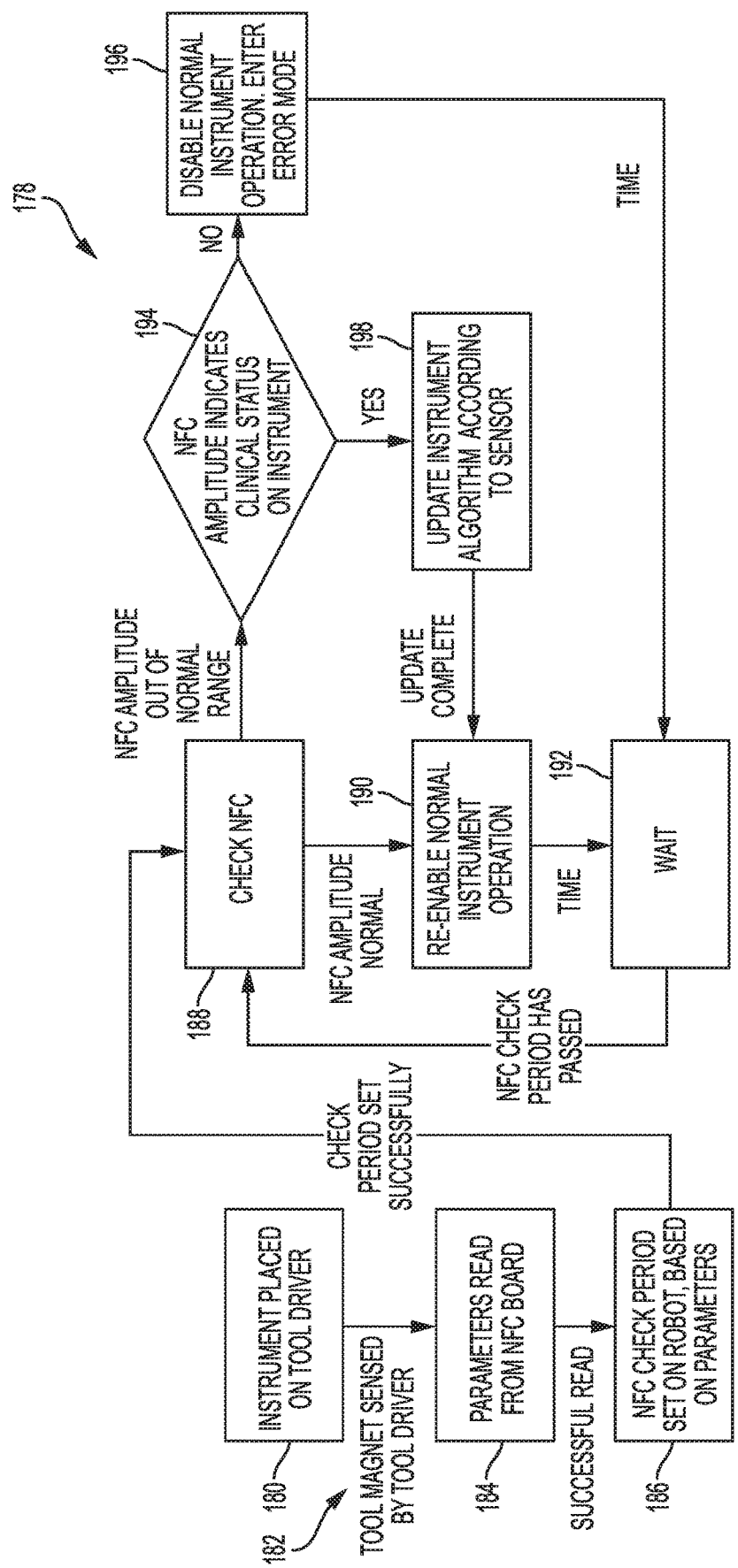
FIG. 30 is a flowchart of another embodiment of a method including communication from a surgical tool to a robotic surgical system.

FIG. 30 illustrates another embodiment of a method 178 of using a surgical tool that includes at least one door (or other switch control mechanism) configured to be selectively opened and closed to move the surgical tool between different modes of communication with a robotic surgical system to which the tool 10 is releasably and replaceably coupled. The method 160 of FIG. 29 is a scenario where a surgical tool has two modes of communication, e.g., includes one door (or other switch control mechanism). The method of FIG. 30 is a scenario where a surgical tool has more than two modes of communication, e.g., includes a first door (or other switch control mechanism) and a second door (or other switch control mechanism).

In general, in the method 178 there are two abnormal modes of communication for the surgical tool in addition to a normal mode of communication for the tool. The tool thus has three modes of communication in this illustrated embodiment. If the communication signal from the tool to the robotic surgical system is indicative of a first error state, e.g., the signal is within a first amplitude range, then the robotic surgical system modifies the clinical operation of the tool to reflect this state. If the communication signal from the tool to the robotic surgical system is indicative of a second error state, e.g., the signal is within a second amplitude range that is different from the first amplitude range, then the robotic surgical system disables normal operation of the tool and enters an error mode. For example, if in the method 160 the surgical tool is a stapler and a staple cartridge is not present in the tool's end effector and a user opens a first door of the tool (or activates another type of switch control mechanism), the first error state is triggered and the robotic surgical system, e.g., a control system thereof, configures itself to prevent staple firing. If a cartridge is subsequently properly loaded into the end effector, the robotic surgical system detects that the tool is operating normally instead of operating in the first error state and thus configures itself to allow staple firing. If a user opens a second door of the tool (or activates another type of switch control mechanism), the second error state is triggered and the robotic surgical system disables normal operation of the tool because the robotic surgical system cannot communicate with the tool.

More particularly, in the method 178 the tool is removably coupled 180 to the robotic surgical system similar to the coupling 162 of FIG. 29, the coupling 180 is sensed 182 by the robotic surgical system similar to the sensing 164 of FIG. 29, the robotic surgical system reads 184 parameters of the tool similar to the parameter reading 166 of FIG. 29, and the robotic surgical system sets 186 a schedule for NFC communication checks with the tool based on the parameters of the tool similarly to the setting 168 of FIG. 29. When the robotic surgical system communicates via NFC with the tool, the robotic surgical system checks 188 the NFC communication from the tool to determine whether or not the communication is normal or abnormal, similar to the checking 170 of FIG. 29. If the communication is determined to be normal then the robotic surgical system enables (or re-enables) 190 normal operation of the tool similar to the enabling/re-enabling 172 of FIG. 29. Time then passes and the robotic surgical system waits 192 for the set 186 time period between NFC communication checks to pass before again checking 188 the NFC communication from the tool.

If, instead, the communication is determined to be abnormal, e.g., if the tool is not operating in the first, normal mode of communication as indicated by an amplitude of the NFC signal from the tool, the robotic surgical system determines 194 an error state of the tool, namely whether or not the NFC communication signal indicates clinical status of the tool. If the tool is operating in a second mode of communication as indicated by an amplitude of the NFC signal from the tool, the robotic surgical system disables 196 normal operation of the tool and enters an error mode in which the robotic surgical system cannot normally operate the tool similar to the disabling 176 of FIG. 29. Time then passes and the robotic surgical system waits 192 for the set 186 time period between NFC communication checks to pass before again checking 188 the NFC communication from the tool. If tool is instead operating in a third mode of communication as indicated by an amplitude of the NFC signal from the tool, the robotic surgical system updates 198 its programmed algorithm as related to the tool accordingly, e.g., to reflect that staple firing should not be performed as in the above example of the method 178. After the update is complete, the robotic surgical system re-enables 190 normal operation and waits 192 for the set 186 time period between NFC communication checks to pass before again checking 188 the NFC communication from the tool. The robotic surgical system may thus regularly monitor the status of the tool regardless of whether the tool is operating normally or abnormally so the robotic surgical system can adjust its control of the tool as needed based on the tool's current status. If the tool has more modes of communication than those depicted in the method 178 of FIG. 30, the robotic surgical system's determining 194 would include checking for the additional mode(s) with resulting actions taken by the robotic surgical system as appropriate, e.g., updating its programmed algorithm for the tool in a different way than in the updating 198.

As discussed above, the control systems disclosed herein can be implemented using one or more computer systems, which may also be referred to herein as digital data processing systems and programmable systems.

One or more aspects or features of the control systems described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

Figure 31:
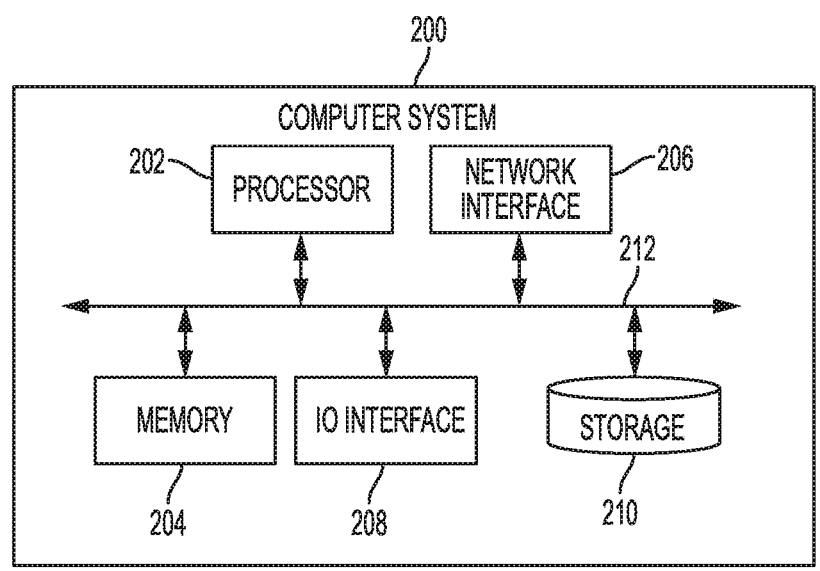
FIG. 31 is a schematic view of one embodiment of a computer system.

FIG. 31 illustrates one exemplary embodiment of a computer system 200. As shown, the computer system 200 includes one or more processors 202 which can control the operation of the computer system 200. "Processors" are also referred to herein as "controllers." The processor(s) 202 can include any type of microprocessor or central processing unit (CPU), including programmable general-purpose or special-purpose microprocessors and/or any one of a variety of proprietary or commercially available single or multi-processor systems. The computer system 200 can also include one or more memories 204, which can provide temporary storage for code to be executed by the processor(s) 202 or for data acquired from one or more users, storage devices, and/or databases. The memory 204 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 200 can be coupled to a bus system 212. The illustrated bus system 212 is an abstraction that represents any one or more separate physical busses, communication lines/interfaces, and/or multi-drop or point-to-point connections, connected by appropriate bridges, adapters, and/or controllers. The computer system 200 can also include one or more network interface(s) 206 that enable the computer system 200 to communicate with remote devices, e.g., motor(s) coupled to the drive system that is located within the surgical device or a robotic surgical system, one or more input/output (IO) interface(s) 208 that can include one or more interface components to connect the computer system 200 with other electronic equipment, such as sensors located on the motor(s), and one or more storage device(s) 210. The storage device(s) 210 can include any conventional medium for storing data in a non-volatile and/or non-transient manner. The storage device(s) 210 can thus hold data and/or instructions in a persistent state, i.e., the value(s) are retained despite interruption of power to the computer system 200.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
    a surgical tool including an elongate shaft, an end effector at a distal end of the elongate shaft, and a housing at a proximal end of the elongate shaft; wherein:
    the surgical tool is configured to transmit a near field communication (NFC) signal to a robotic surgical system in a mode of communication based on a position of a door in the housing;
    the surgical tool is configured to transmit the NFC signal in a first mode of communication with the door being open, the first mode of communication being indicative of the surgical tool operating in a first state of operation; and
    the surgical tool is configured to transmit the NFC signal in a second mode of communication with the door being closed, the second mode of communication being indicative of the surgical tool operating in a second state of operation.

2. The system of claim 1, wherein the surgical tool includes a switch configured to be open with the door open and to be closed with the door closed.

3. The system of claim 2, wherein with the switch being open the surgical tool is configured to communicate with the robotic surgical system at a first frequency, and with the switch being closed the surgical tool is configured to communicate with the robotic surgical system at a second frequency that is different from the first frequency.

4. The system of claim 1, wherein the door is configured to be manually opened and closed.

5. The system of claim 1, wherein the first state of operation is indicative of the surgical tool operating normally, and the second state of operation is indicative of the surgical tool operating in an error state.

6. The system of claim 1, wherein the surgical tool is configured to receive a control signal from a robotic surgical system, and the surgical tool is configured to releasably and replaceably couple to the robotic surgical system.

7. The system of claim 1, further comprising the robotic surgical system;
    wherein the robotic surgical system is configured to transmit a signal to the surgical tool; and
    wherein, based on a response of the surgical tool to the transmitted signal, determining whether the surgical tool is operating in the first state, in which the surgical tool is operating normally, or the second state, in which the surgical tool is operating in an error state.

8. The system of claim 7, wherein the response of the surgical tool includes a second NFC signal transmitted from the surgical tool to the robotic surgical system, and the determining includes determining whether an amplitude of the second NFC signal is within a first amplitude range corresponding to the first state or if the second NFC signal is within a second, different amplitude range corresponding to the second state.

9. A surgical system, comprising:
    a surgical tool including an elongate shaft, an end effector at a distal end of the elongate shaft, and a housing at a proximal end of the shaft; wherein:

the housing is configured to releasably and replaceably couple to a robotic surgical system;

with a door in the housing closed, the surgical tool is configured to transmit a near field communication (NFC) signal to the robotic surgical system; and with the door in the housing open, the surgical tool is prevented from transmitting any NFC signals to the robotic surgical system.

10. The system of claim 9, wherein the surgical tool includes a switch configured to be open with the door open and to be closed with the door closed.

11. The system of claim 10, wherein the surgical tool includes an antenna configured to transmit the NFC signal to the robotic surgical system;

the switch being closed allows the antenna to communicate with the robotic surgical system; and the switch being open shorts a circuit of the surgical tool such that the antenna cannot communicate with the robotic surgical system.

12. The system of claim 9, wherein the door is configured to be manually opened and closed.

13. The system of claim 9, further comprising the robotic surgical system;

wherein the robotic surgical system is configured to transmit a signal to the surgical tool; and wherein, based on a response of the surgical tool to the transmitted signal, the robotic surgical system is configured to determine whether the surgical tool is operating in a first state, in which the surgical tool is operating normally, or a second state, in which the surgical tool is operating in an error state.

14. The system of claim 13, wherein the response of the surgical tool is a lack of a response signal transmitted from the surgical tool to the robotic surgical system, and the determining includes determining that the surgical tool is operating in the second state due to the lack of the response signal.

15. The system of claim 14, wherein, the robotic surgical system is configured to, in response to determining that the surgical tool is operating in the second state, adjust a parameter of the robotic surgical system that controls future transmission of signals from the robotic surgical system to the surgical tool.

16. The system of claim 15, wherein the adjustment of the parameter disables the future transmission of signals from the robotic surgical system to the surgical tool.

17. The system of claim 15, wherein the second state is indicative of the surgical tool operating in an error state; and the adjustment of the parameter disables the future transmission of signals from the robotic surgical system to the surgical tool related to the error state and allows the future transmission of signals from the robotic surgical system to the surgical tool that are not related to the error state.

18. A surgical system, comprising:

a surgical tool including an elongate shaft, an end effector at a distal end of the elongate shaft, a housing at a proximal end of the shaft, a switch control mechanism, a switch, and a circuit; wherein:

the housing is configured to releasably and replaceably couple to a robotic surgical system;

the switch control mechanism is configured to move between first and second positions relative to the housing;

the movement of the switch control mechanism from the first position to the second position is configured to cause the switch to close the circuit, the circuit being closed allowing the surgical tool to communicate with the robotic surgical system; and the movement of the switch control mechanism from the second position to the first position is configured to cause the switch to open the circuit, the circuit being open preventing the surgical tool from communicating with the robotic surgical system.

19. The system of claim 18, wherein the surgical tool includes an antenna configured to communicate with the robotic surgical system using near field communication (NFC) with the switch control mechanism in the second position.

20. The system of claim 18, wherein the switch control mechanism includes a door in the housing.

* * * * *